(12) United States Patent
Case et al.

(10) Patent No.: US 10,489,940 B2
(45) Date of Patent: Nov. 26, 2019

(54) SYSTEM AND COMPUTER-IMPLEMENTED METHOD FOR IMPROVING IMAGE QUALITY

(71) Applicant: Cardiovascular Imaging Technologies, L.L.C., Kansas City, MO (US)

(72) Inventors: James Arthur Case, Kansas City, MO (US); Paul O'Connell Case, Kansas City, MO (US); Timothy Murray Bateman, Leawood, KS (US); Paul Andrew Helmuth, Shawnee, KS (US)

(73) Assignee: Cardiovascular Imaging Technolgies, L.L.C., Kansas City, MO (US)

( * ) Notice: Subject to any disclaimer, the term of this patent is extended or adjusted under 35 U.S.C. 154(b) by 72 days.

(21) Appl. No.: 15/695,855

(22) Filed: Sep. 5, 2017

(65) Prior Publication Data

US 2019/0073802 A1 Mar. 7, 2019

(51) Int. Cl.
| | |
|---|---|
| *G06K 9/00* | (2006.01) |
| *G06T 11/00* | (2006.01) |
| *G06T 7/30* | (2017.01) |
| *G06T 3/00* | (2006.01) |
| *A61B 6/03* | (2006.01) |

(Continued)

(52) U.S. Cl.
CPC ........... *G06T 11/005* (2013.01); *A61B 6/037* (2013.01); *A61B 6/5205* (2013.01); *G06T 3/0068* (2013.01); *G06T 5/002* (2013.01); *G06T 7/30* (2017.01); *A61B 6/5258* (2013.01); *G06T 2207/10104* (2013.01); *G06T 2207/10108* (2013.01); *G06T 2207/20081* (2013.01); *G06T 2207/30004* (2013.01); *G06T 2207/30241* (2013.01); *G06T 2211/424* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,319,551 A | * | 6/1994 | Sekiguchi | G06T 5/20 |
| | | | | 382/131 |
| 2006/0237652 A1 | * | 10/2006 | Kimchy | A61B 1/05 |
| | | | | 250/363.02 |

(Continued)

*Primary Examiner* — Jose L Couso
(74) *Attorney, Agent, or Firm* — Hovey Williams LLP

(57) ABSTRACT

A system and computer-implemented method for improving the quality of images, such as images used in medical diagnosis. In a first technique, sinogram data, intermediate volumes, and transmission CT-based attenuation correction files are created. Scatter correction is performed, and a scatter correction map is created. Misregistration offsets are measured, and a correction registration mask is created using volume reprojection. The two masks are combined and applied to create the enhanced image data. In a second technique, a difference may be determined for each parent and child pixel pair, and an average difference may be determined for all pairs. For each pair which is under the average difference, the child may be eliminated and replaced with a new child. This process may be iteratively repeated, with the image data being incrementally enhanced with each iteration. For both techniques, the enhanced image data may be communicated to an interpretive application for display.

10 Claims, 7 Drawing Sheets

(51) Int. Cl.
*A61B 6/00* (2006.01)
*G06T 5/00* (2006.01)

(56) References Cited

U.S. PATENT DOCUMENTS

| | | | | |
|---|---|---|---|---|
| 2009/0225932 A1* | 9/2009 | Zhu | ............... | A61B 6/032 |
| | | | | 378/7 |
| 2011/0150306 A1* | 6/2011 | Ross | ............... | A61B 6/032 |
| | | | | 382/131 |
| 2012/0263360 A1* | 10/2012 | Zhu | ............... | G06T 5/002 |
| | | | | 382/131 |
| 2013/0248719 A1* | 9/2013 | Volokh | ............... | A61B 6/037 |
| | | | | 250/362 |
| 2014/0270448 A1* | 9/2014 | Mok | ............... | A61B 6/5264 |
| | | | | 382/131 |
| 2015/0348289 A1* | 12/2015 | Ida | ............... | A61B 6/032 |
| | | | | 382/131 |
| 2018/0203140 A1* | 7/2018 | Miao | ............... | G01T 1/2985 |

* cited by examiner

SYSTEM AND COMPUTER-IMPLEMENTED METHOD FOR IMPROVING IMAGE QUALITY

FIELD

The present invention relates to systems and methods for processing images, and more particularly, embodiments concern a system and computer-implemented method for improving the quality of images by employing iterative reprojection of reconstructed datasets to correct misregistration of transmission and emission datasets in images, and/or by employing a "genetic" artificial intelligence technique.

BACKGROUND

Positron emission tomography (PET) and single photon emission computed tomography (SPECT) are medical imaging techniques used to observe metabolic processes in the body. Both techniques detect gamma rays emitted indirectly by the decay of a radionuclide (tracer) which is introduced into the body on a biologically active molecule. PET tracers employ radioactive isotopes that emit positrons that secondarily decay through complete annihilation with electrons in the media: emitting two photons traveling in opposite directions. SPECT tracers employ radioactive isotopes that upon decay emits a single photon. Both PET and SPECT imaging are referred to as "nuclear medicine". Three-dimensional images (reconstructions) of the concentrations of the tracer within the body are then constructed by a computer program. The final images depict physiological processes that can predict the presence of disease.

One of the most confounding artifacts in nuclear medicine is attenuation. Attenuation occurs when gamma rays are absorbed within the patient prior to detection by the imaging system. Attenuation artifact reduces clinical confidence, alters quantitative accuracy and can lead to misdiagnoses. To perform attenuation correction, two datasets are required: a map of the patient's anatomy (the attenuation map) and the uncorrected emission data. The attenuation map can be acquired either with a computed tomography (CT) scan or an external radioactive source. The emission data and attenuation map can be combined in a mathematical algorithm to compensate for the influence of attenuation. In most instances, the emission data and attenuation map are acquired sequentially. Patient motion between the emission data and attenuation map can lead to incomplete or inaccurate attenuation correction.

Image registration is the process of aligning the emission data and attenuation maps prior to performing attenuation correction. Misregistration of the transmission and emission datasets is a primary source of inaccurate attenuation correction in PET and SPECT images. For conventional reconstruction approaches, correction for misregistration must be performed prior to emission reconstruction. This requires the raw unreconstructed and uncorrected "sinogram" data be available. Most modern PET/CT and SPECT systems do not export a raw sinogram dataset that can be used for reconstruction and therefore if inaccurate misregistration correction has been applied, users would have to reprocess the data at the acquisition workstation. If the raw sinogram data is lost, deleted, or unavailable, studies with inaccurate misregistration correction are unusable clinically.

Another source of artifact is the presence of image noise. Image noise occurs when the random variations in the signal can be perceived by the clinician. Though this can be overcome by increasing the amount of radiation utilized, this comes at the expense of increasing the patient's overall radiation exposure, and thereby increasing the possibility of inducing future cancers. Most nuclear medicine imaging protocols require using the minimum radiation dose for performing a clinical task. To reduce image noise, the image data can be smoothed with image filters to preferentially reduce image noise while preserving the features of the image.

Most image noise filters rely on a simple spatial or frequency based filtering kernel that does not take into account the inherent feature of the image. This has the result of sacrificing image contrast to obtain greater degrees of noise control. This loss of contrast can result in masking true physiological defects and potentially missing disease. Most image processing programs employ either a frequency based noise filter, such as a low pass filter that preferentially preserves large objects in the image or a spatial based filter that performs weighted averaging across an image. More sophisticated filters can use an artificial intelligence (AI) technique that allows the program to enhance desirable features of an image while suppressing less desirable features. These AI-based filters, though useful, often require large amounts of computer processing power and are not easily translated onto conventional computer workstations.

This background discussion is intended to provide information related to the present invention which is not necessarily prior art.

SUMMARY

Embodiments of the present invention solve the above-described and other problems and limitations by providing a system and computer-implemented method for improving the quality of images, such as PET or SPECT images, by employing iterative reprojection of reconstructed datasets to correct misregistration of transmission and emission datasets in images, and/or by employing a genetic artificial intelligence technique. Either or both techniques may be used, in the example context of medical imagery, to significantly reduce the risk of medical misdiagnoses.

In a first embodiment of the present invention, a computer-implemented method may be provided for improving the functioning of a computer for enhancing initial image data. The computer-implemented method may be performed by a computing device, and may broadly comprise the following. Initial image data may be loaded from an imaging device, including creating sinogram data, creating intermediate volumes, and creating transmission CT-based attenuation correction files. Scatter correction may be performed, including creating a scatter correction map. One or more misregistration offsets may be measured. A correction registration mask may be created using volume reprojection. The correction registration mask may be combined with the scatter mask. The combined correction registration mask and scatter mask may be applied to correct the initial image data to create the enhanced image data. The enhanced image data may be communicated to an interpretive application for display.

Various implementations of the foregoing first embodiment may include any one or more of the following additional features. The initial image data may be generated by a medical imaging device, such as a PET or SPECT imaging device, and the enhanced image data may be used to diagnose a medical condition. The correction registration mask may be created using an attenuation corrected reconstructed emission dataset, a non-attenuation corrected reconstructed emission data set, and a computed tomography or line source attenuation map. The method may further include filtering the enhanced image data to reduce noise prior to communicating the enhanced image data to the interpretive application.

Performing scatter correction may include the following. An image space may be reconstructed from the initial image data. A probability field may be created for a Monte-Carlo look-up. A Monte-Carlo technique may be employed iteratively to simulate a first order scatter component from a scatter contaminated emission sinogram. A random coincident event may be created, and whether the coincident event is a prompt gamma may be determined. A progress of a photon may be followed as the photon is scattered or reaches an edge of an imaging field, and a progress of the coincident photon may be followed until the coincident photon until it scatters or reaches an edge of the imaging field. Each unscattered photon may be identified. A new trajectory for each scattered photon that is not a prompt gamma may be defined, and a progress of the photon on the new trajectory may be followed until the photon scatters or reaches the edge of the imaging field. A random angle for each scattered photon that is a prompt gamma may be created. A scatter estimate for each random event may be created to compensate for scatter. The scatter correction map may be created.

In a second embodiment of the present invention, a computer-implemented method may be provided for improving the functioning of a computer for enhancing initial image data. The computer-implemented method may be performed by a computing device, and may broadly comprise the following steps. Collections of pairs of pixels may be created from the initial image data, with each pair of pixels including a parent pixel and a child pixel. The number of pairs created form an image is a user input to the technique. A pair difference may be determined for each pair of pixels. An average difference may be determined over all pairs of pixels. For of those pairs of pixels a pair difference greater than the average difference, the child pixel may be eliminated, replacing the eliminated child pixel with a new pixel from the parent pixel. The foregoing steps may be repeated for a predetermined number of iterations, during which the image data is incrementally enhanced with each iteration. The enhanced image data may be communicated to an interpretive application for display.

Various implementations of the foregoing second embodiment may include any one or more of the following additional features. The initial image data may be generated by a medical imaging device, such as a PET or SPECT imaging device, and the enhanced image data may be used to diagnose a medical condition. The child pixel may be selected from a plurality of pixels located within a defined area from the parent pixel. The predetermined number of iterations may be greater than fifteen.

This summary is not intended to identify essential features of the present invention, and is not intended to be used to limit the scope of the claims. These and other aspects of the present invention are described below in greater detail.

DRAWINGS

Embodiments of the present invention are described in detail below with reference to the attached drawing figures, wherein.

Figure 1:
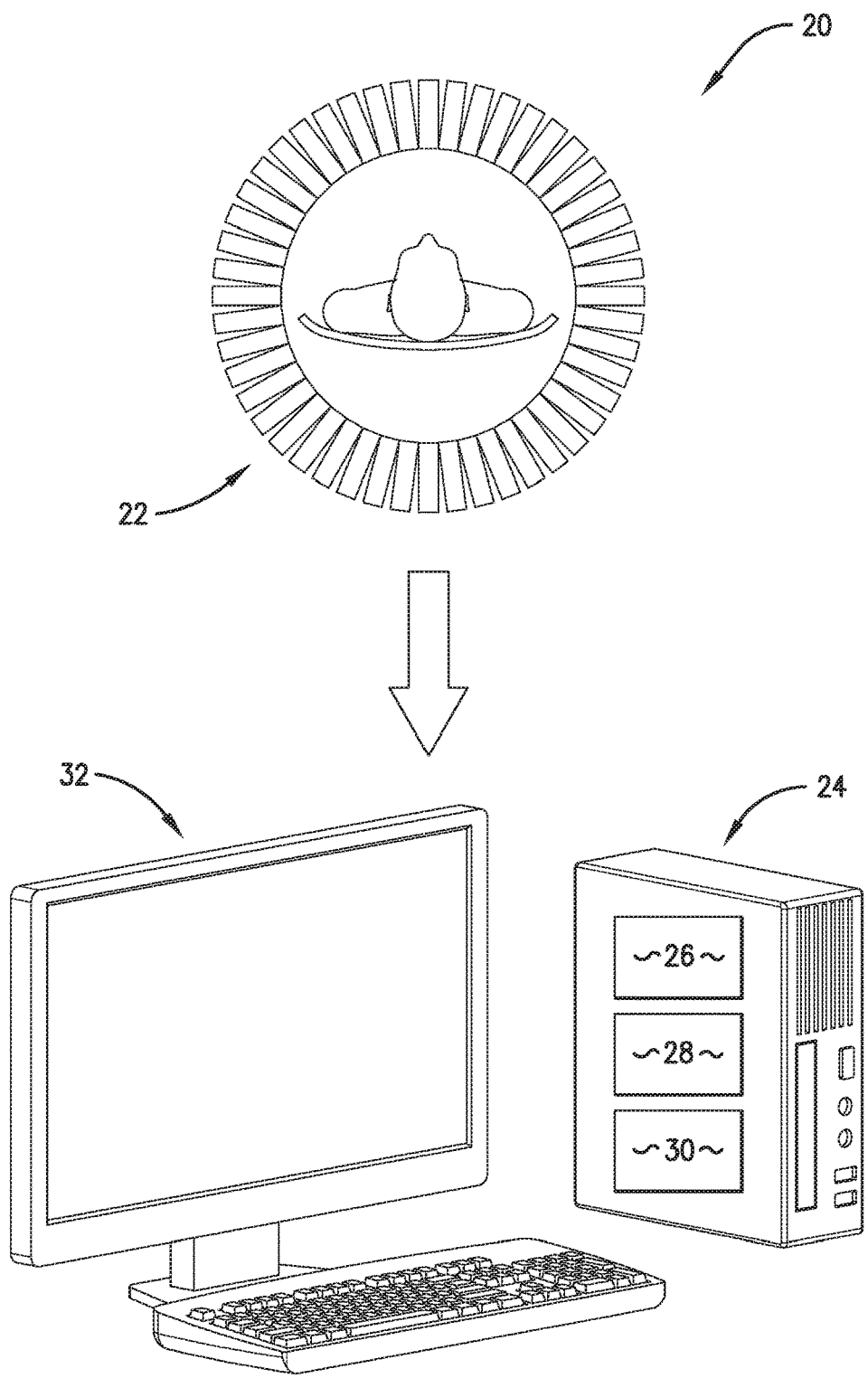
FIG. 1 is a high level diagram of an embodiment of a system for improving the quality of images.

The figures are not intended to limit the present invention to the specific embodiments they depict. The drawings are not necessarily to scale.

DETAILED DESCRIPTION

The following detailed description of embodiments of the invention references the accompanying figures. The embodiments are intended to describe aspects of the invention in sufficient detail to enable those with ordinary skill in the art to practice the invention. Other embodiments may be utilized and changes may be made without departing from the scope of the claims. The following description is, therefore, not limiting. The scope of the present invention is defined only by the appended claims, along with the full scope of equivalents to which such claims are entitled.

In this description, references to "one embodiment", "an embodiment", or "embodiments" mean that the feature or features referred to are included in at least one embodiment of the invention. Separate references to "one embodiment", "an embodiment", or "embodiments" in this description do not necessarily refer to the same embodiment and are not mutually exclusive unless so stated. Specifically, a feature, structure, act, etc. described in one embodiment may also be included in other embodiments, but is not necessarily included. Thus, particular implementations of the present invention can include a variety of combinations and/or integrations of the embodiments described herein.

Broadly characterized, embodiments of the present invention provide a system and computer-implemented method for improving the quality of images, such as PET and SPECT images, by employing iterative reprojection of reconstructed datasets to correct misregistration of transmission and emission datasets in images and/or by employing an genetic artificial intelligence image filtering technique, either or both of which may be used, in the example context of medical imaging, to significantly reduce the risk of medical misdiagnoses. This technique creates a more representative distribution of the activity by reducing common image artifacts without sacrificing image contrast. Though described herein primarily in the example context of medical imaging, the present technology is not limited to medical imaging and may be adapted for use with other types of images.

In more detail, a first embodiment may employ iterative reprojection of reconstructed datasets to correct misregistration artifacts that are a result of misalignment of the attenuation map and emission data. Specifically, this embodiment could be applied on emission data that had already been reconstructed with misaligned emission and transmission data.

A second embodiment, which may be used by itself or in combination with the first embodiment, may include a "genetic" artificial intelligence (AI) technique for enhancing the quality of reconstructed images by recognizing patterns that are intrinsic to the images. The AI technique may use a set of evolutionary rules combined with a randomly created set of "individuals" to search for the optimal individual, which is, in this context, a pixel, who is best suited to survive under the evolutionary rules. By removing those individuals who are less suited for survival, mutating the survivors to create "child" pixel pairs, and repeating this process for multiple generations, an optimal set of pixel associations can be achieved.

Referring to FIG. 1 an embodiment of a system 20 and an exemplary environment in which the system 20 may operate is shown for improving the quality of images by employing iterative reprojection of reconstructed datasets to correct misregistration of transmission and emission datasets in images, and/or by employing a genetic artificial intelligence technique. The system 20 may broadly comprise a PET or SPECT imaging device 22; a computing device 24 including an electronic memory element 26, an electronic processing element 28, and an electronic communication element 30; and a display device 32.

The PET or SPECT imaging device 22 may be substantially any suitable conventional or non-conventional PET or SPECT scanners configured to generate PET or SPECT images which are amenable to improvement by the present technology. The computing device 24 may be substantially any suitable computer configured or configurable to perform the functions, including the steps of the computer-implemented method discussed below, set forth herein for improving the quality of the images generated by the PET or SPECT imaging device 22. In particular, the memory element 26 may receive and store the initial images and other data; the processing element 28 may perform various actions to enhance the quality of the initial images stored in the memory element 26, and may apply interpretive software to the improved images; and the communication element 30 may, as necessary or desired, transmit the enhanced images to another location for storage, use, and/or further processing. The display device 32 may be substantially any suitable display for visually representing the enhanced images or aspects thereof.

In operation, the system 20 may broadly function substantially as follows. Referring also to FIGS. 2-7, in a first embodiment, the system 20 may be used to enhance initial image data, wherein the initial image data may be generated by a medical imaging device, such as the PET or SPECT imaging device 22, and the enhanced image data may be used to diagnose a medical condition. Initial image data may be loaded from an imaging device, as shown in 122, including creating sinogram data, as shown in 142, creating intermediate volumes (attenuation corrected and non-attenuation corrected emission volumes), as shown in 144, and creating transmission (CT or line source) based attenuation correction files, as shown in 154. Scatter correction may be performed, as shown in 126, including creating a scatter correction maps, as shown in 194. One or more misregistration offsets may be measured, as shown in 164. A correction registration mask may be created using the iterative reprojection technique, as shown in 196. The correction registration mask may be combined with the scatter mask, as shown in 198. The combined correction registration mask and scatter mask may be applied to correct the initial image data to create the enhanced image data, as shown in 200. The enhanced image data may be communicated to an interpretive application for display, as shown in 204.

Figure 8:
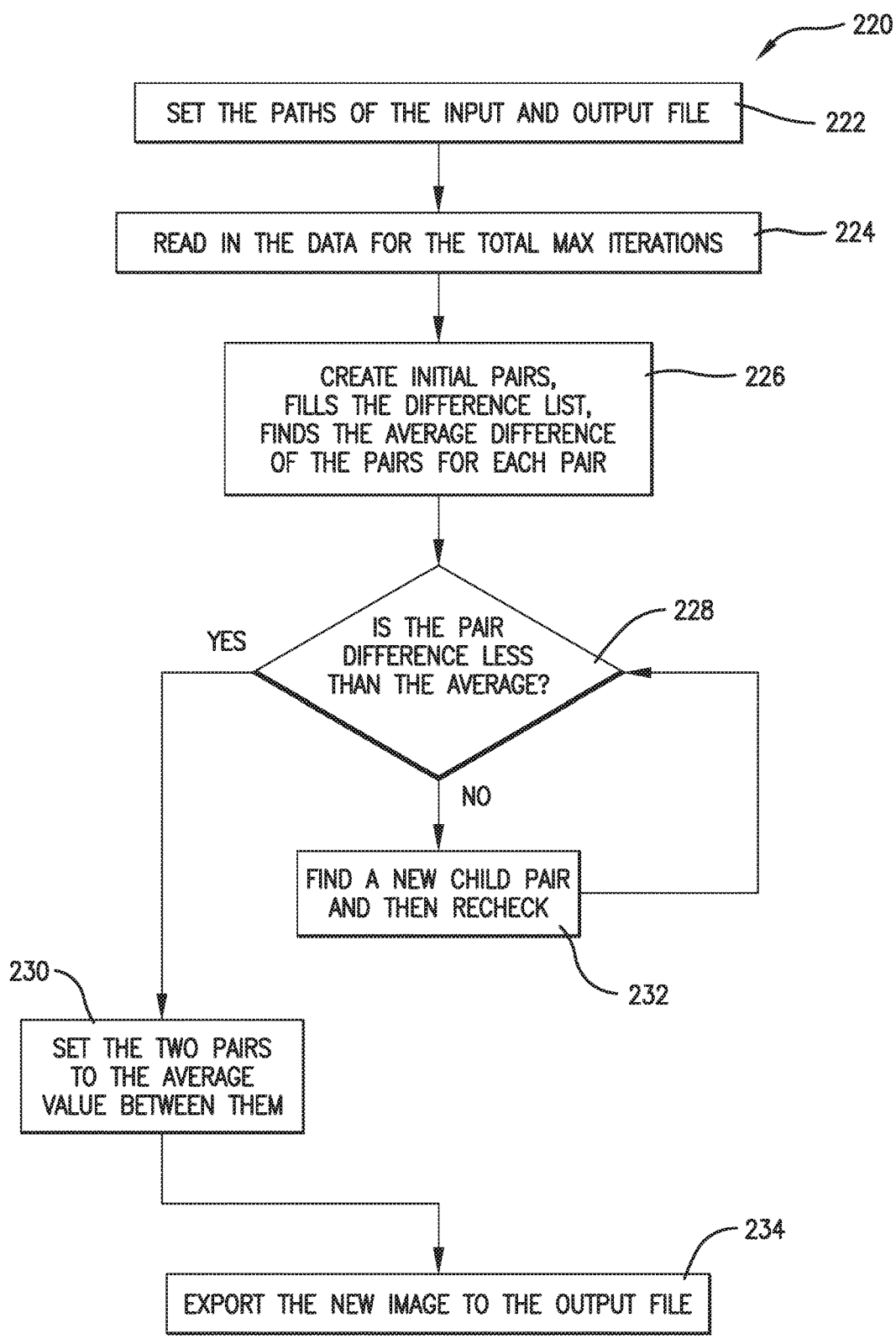
FIG. 8 is a flowchart of a second embodiment of a computer-implemented method for improving the quality of images using a genetic artificial intelligence technique, wherein the computer-implemented method may be performed by the system of FIG. 1.

Referring also to FIG. 8, in a second embodiment the system 20 may be used to enhance initial image data, wherein the initial image data may be generated by a medical imaging device, such as the PET or SPECT imaging device 22, and the enhanced image data may be used to diagnose a medical condition. A defined number of pairs of pixels may be created from the initial image data, with each pair of pixels including a parent pixel and a child pixel, as shown in 226. A pair difference may be determined for each pair of pixels, as shown in 226. An average difference may be determined for all pairs of pixels, as shown in 226. For each pair of pixels having a pair difference which is greater than the average difference, the child pixel may be eliminated, replacing the eliminated child pixel with a new pixel from the parent pixel pair, as shown in 232 offset from the parent within a defined area. Parent pixels are those pixels for which the differences are less that the average difference. The foregoing steps may be repeated for a predetermined number of iterations, during which the image data is incrementally enhanced with each iteration. The enhanced image data may be communicated to an interpretive application for display, as shown in 234.

The system 20 may include more, fewer, or alternative components and/or perform more, fewer, or alternative actions, including those discussed elsewhere herein, and particularly those discussed in the following section describing the computer-implemented method.

Referring again to FIGS. 2-7, a first embodiment of a computer-implemented method 120 is shown for improving the functioning of a computer, such as the computing device 24 of the system 20, for improving the quality of an image by employing iterative reprojection of reconstructed datasets to correct misregistration and/or to correct scatter in transmission and emission datasets in the image, may apply prompt gamma correction for reconstructed Rb-82 data, and/or may use GPU processing to accelerate reconstruction times. This first embodiment may be used by itself or in combination with the second embodiment described below. It will be appreciated that computer-implemented method 120 may be a corollary to the functionality of the system 20, and may be performed by the system 20 or a suitable version thereof.

Broadly, initial steps, such as data acquisition steps, may be performed by the PET or SPECT imaging device 22 and involve software that is native to that device 22. These initial steps may include acquiring PET or SPECT image data, performing CT or line source attenuation correction, performing raw data corrections, and exporting the results to the system 20 and computer-implemented method 120 implementing the present technology. Thereafter, raw projection data may be received in the form of the exported PET volume data files from the imaging device 22, corrected for misregistration and scatter, and filtered. The volume reprojection and restoration process used by the system 20 may be an iterative forward and backprojection approach for creating a correction mask for the reconstructed data. The forward projection process uses a sum of all of the counts along the line of site of the detector to create a 2D projection of the 3D volume. This process is repeated for a large number of projection angles around the patient. The forward projection process may also be weighted by the attenuation map to create an attenuated forward projection set. The process may use four datasets for creating this mask: (1) an attenuation corrected reconstructed emission data (with or without scatter correction) that has not been corrected for misregistration, (2) a non-attenuation corrected reconstructed emission data (without scatter correction), and (3) a CT or line source attenuation map without the misregistration offsets applied, and (4) a CT or line source attenuation map with the misregistration offsets applied. For each of these volume maps, the technique creates a forward projected representation of the volume map. Emission data may or may not be ECG gated.

The forward projected sinograms of the non-attenuation corrected emission data is corrected for the attenuation using an un-shifted transmission forward projection dataset ("simulated misregistered sinogram"). The simulated misregistered sinogram is then reconstructed using an iterative reconstruction and the forward projection of the attenuation corrected reconstructed emission data (with or without scatter correction) that has not been corrected for misregistration. The result is a misregistration contaminated volume that has been reconstructed using the forward projection of the misregistration contaminated original emission volumes ("uncorrected simulated volume"). This creates the simulated misregistered volume.

The forward projected sinograms of the non-attenuation corrected emission data is corrected for the attenuation using a shifted (misregistration corrected) transmission forward projection dataset. The corrected forward projection dataset is then reconstructed using an iterative reconstruction and the forward projection of the attenuation corrected reconstructed emission data (with or without scatter correction) that has been corrected for misregistration. The result is a misregistration corrected volume that has been reconstructed using the forward projected emission volumes created without attenuation correction ("misregistration corrected simulated volume").

These volumes (uncorrected simulated volume and the misregistration corrected simulated volume) are then forward projected into sinogram views ("uncorrected simulated sinogram" and "misregistration corrected simulated sinogram"). The original non-attenuation corrected sinogram is then corrected for attenuation using the shifted transmission sinogram. It may also be corrected for photon scatter and prompt gamma photons. This corrected sinogram is then divided by the uncorrected simulated sinogram. The ratio is then backprojected to create a map of correction factors that would corrected for misregistration present in the original attenuation corrected volume. This process is repeated iteratively to improve the corrections estimate. A flowchart of the technique is given in FIG. 9.

In a test of this exemplary employment, a Data Spectrum Anthropomorphic Phantom with a uniform activity distribution in the myocardium was acquired on a PET/CT system. Emission datasets (AC and non-AC) were created with no misregistration artifact and with a twenty millimeter misregistration artifact in a two hundred fifty-six by two hundred fifty-six slice volume. Circumferential profiles were taken at the apex, mid, and base of the myocardium at twelve degree intervals. In the region of the misregistration artifact, myocardial counts were reduced by thirty-two percent, thirty-four percent, and twenty-one percent in the apex, mid, and base respectively. After iterative reprojection correction (IRC), all regions were within ten percent of the misregistration free reconstruction. This exemplary employment does not require sinogram data, and can be applied to 3D data post.

The misregistration mask can be exported containing a pixel-by-pixel factor for correcting for misregistration. This mask can also be combined with a scatter correction mask for removing scatter and prompt gamma contamination.

Figure 6:
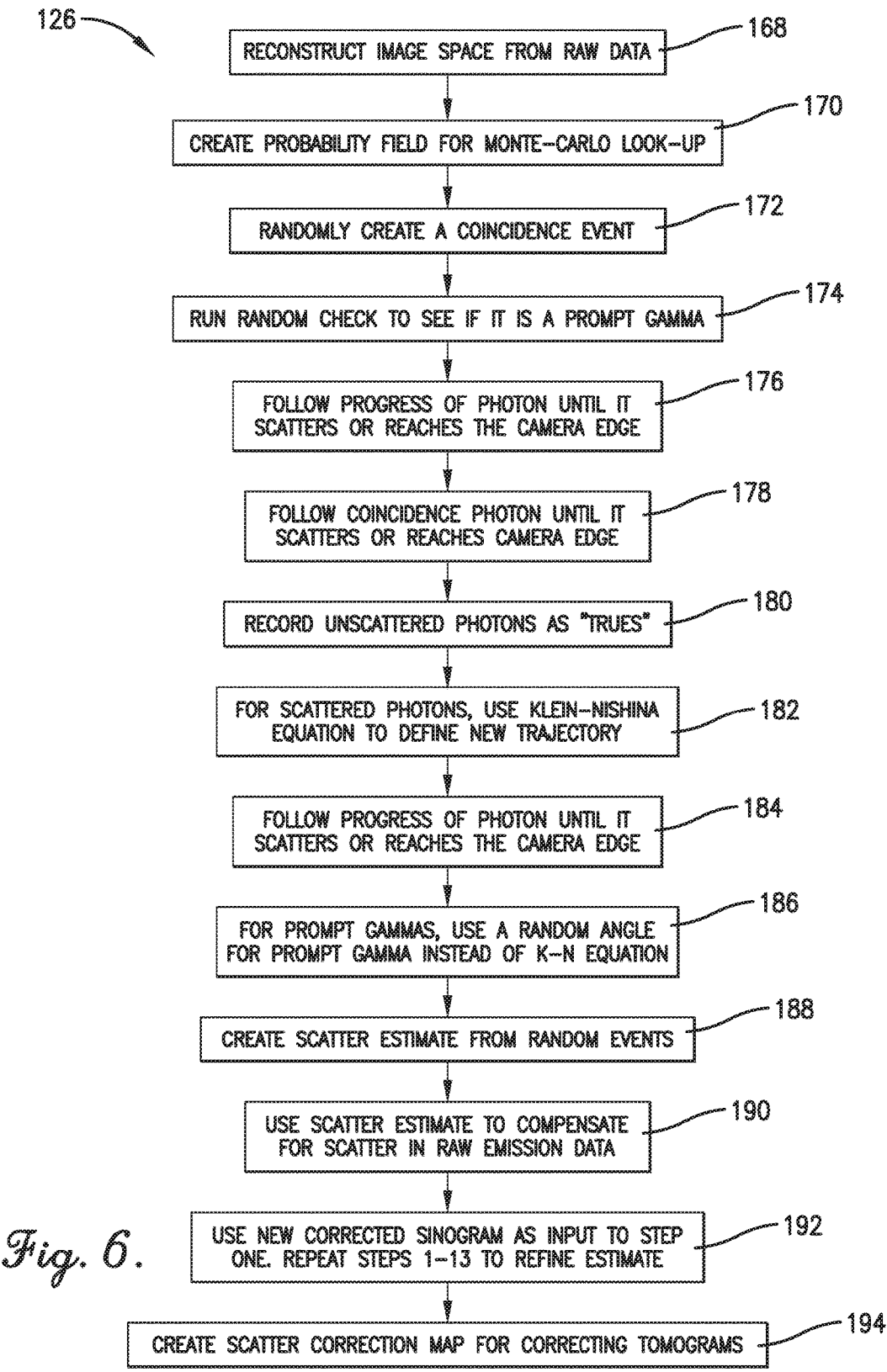
FIG. 6 is a flowchart of a scatter correction aspect of the computer-implemented method of FIG. 2.

Referring to FIG. 6, the correction of scatter, from step 126, may include the following steps. The creation of a probability field, simulation of a large number of virtual annihilation events, determination of the type of event (coincidence or prompt gamma), tracking those events to the detector and incrementing the final scatter sinogram at the detector location where the event arrives.

The reconstructed emission map may be reconstructed from the raw projection data, as shown in 168. A probability map can be create from the reconstructed map by using the sum from the first pixel, for example (0,0,0) to (MAX_X, MAX_Z, MAX_Z) where each pixel value is the sum of all of the preceding pixels. The pixel values are then normalized to the greatest pixel, so that value is in the probability field run from zero to one and are weighted by the count density in the original volume, as shown in 170.

A coincident event may be randomly created, as shown in 172. This is performed by first choosing a random number from zero to one, then tracking that random number to its corresponding value in the probability field described in the preceding paragraph. A random check may be run to see if it is a prompt gamma, as shown in 174. If it is a prompt gamma, the coincidence event is recorded as a random position in the scatter sinogram. The progress of a photon may be followed as it scatters or reaches the camera edge, as shown in 176. The progress of a coincident photon may be followed until it scatters or reaches the camera edge, as shown in 178. Unscattered photons may be recorded as "trues," as shown in 180. For scattered photons, the Klein-Nishina (K-N) equation may be used to define a new trajectory, as shown in 182. The progress of the photon may be followed until it scatters or reaches the camera edge, as shown in 184. For prompt gammas, a random angle may be used instead of the K-N equation, as shown in 186. A scatter estimate may be created for random events, as shown in 188. The scatter estimate may be used to compensate for scatter in the raw emission data, as shown in 190. The estimate may be refined by repeating this process form the beginning using the new corrected sinogram as input, as shown in 192. A scatter correction map and scatter mask may be created for correcting the tomograms, as shown in 194.

For example, scatter events in myocardial perfusion PET imaging degrade image contrast and can introduce unpredictable artifacts. Current analytical techniques for determining the scatter components often fail because of the low signal-to-noise and larger size of cardiac patients. To compensate, the technique embeds Monte-Carlo software. The scatter correction module uses a rapid, iterative Monte-Carlo method for simulating the scatter component from scatter contaminated emission sinograms. The iterative Monte-Carlo technique simulates first order contributions to scatter in the image: (1) scatter events in which one photon is scattered once and the second photon is not scattered, (2) photons scattered into angles where they will be included into the direct plane, and (3) photons where the resulting energy, post scatter, is outside of the minimum energy of the acceptance window of the scanner.

The three-dimensional data may then be exported to another application for further image processing and reconstruction.

Figure 7:
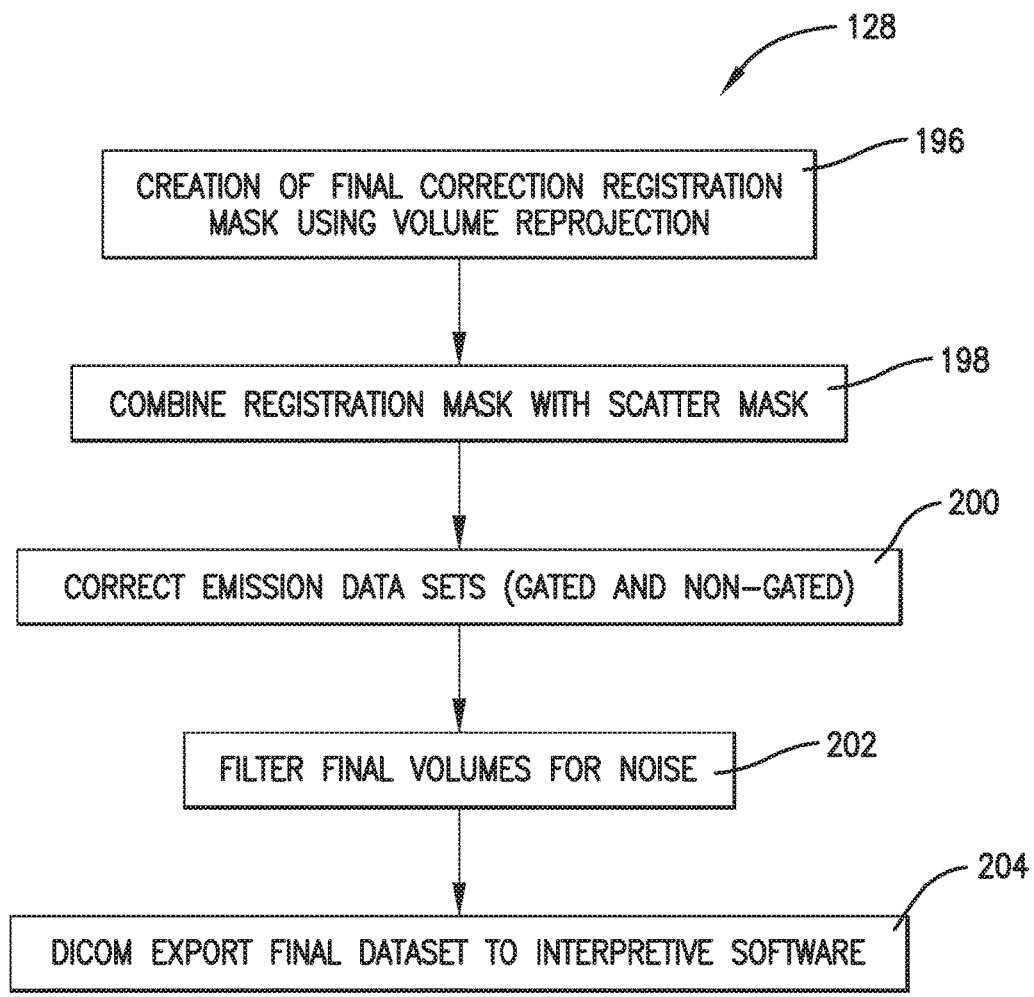
FIG. 7 is a flowchart of a correct volume creation aspect of the computer-implemented method of FIG. 2.

As shown in FIG. 7, the correction of the data and export of the data to the interpretive software, from 128, may include creating the final correction registration mask using volume reprojection, as shown in 196; the registration mask may be combined with the scatter mask, as shown in 198; the emission data sets (gated and non-gated) may be corrected, as shown in 200; the final volumes may be filtered for noise, as shown in 202; and the final dataset may be DICOM exported to the interpretive software, as shown in 204.

In more detail, the virtual sinogram data may be displayed, the registration offsets may be measured, and the reprojection correction and restoration technique may be applied to the emission data. The volume reprojection and restoration technique may use an iterative forward and backprojection approach for creating a correction mask for the reconstructed data. The algorithm may use three datasets for creating this mask: (1) attenuation corrected reconstructed emission data (with or without scatter correction), (2) non-attenuation corrected reconstructed emission data (without scatter correction), and (3) CT or line source attenuation map. The algorithm may then create a set of forward projected datasets using a simple random transform.

An exemplary implementation of this technique may proceed substantially as follows. The CT or transmission map may be converted into scaled attenuation coefficients appropriate for the energy level of the photons. The CT map may be shifted to positions determine form user interface. The CT map, the attenuation corrected emission map, and the non-attenuation emission map may each be forward projected. The non-attenuation corrected sinogram may be calculated using the transmission forward projection to undo the attenuation correction in the forward projected attenuation corrected emission sinogram. A registration correction sinogram may be calculated by comparing the calculated non-attenuation corrected sinogram to the actual forward projected non-attenuation corrected sinogram. A registration correction map may be created by backprojecting the registration correction sinogram. The emission data may be multiplied by the registration correction map to create a registration corrected emission dataset. If necessary, the final dataset may be corrected for misregistration and scatter. The corrected data may be filtered.

Once the data is processed and exported to the interpretative application, the information may be displayed and interpreted by another system or software application. In an example, this process may proceed substantially as follows. Transaxial slices may be reoriented; axial slices may be displayed; perfusion defects may be quantitated; gated data may be displayed; ventricular function may be quantitated; results may be interpreted and reported; and results may be archived.

Referring also to FIG. 8, a second embodiment of a computer-implemented method 220 is shown for improving the functioning of a computer, such as the computing device 24 of the system 20, for improving the quality of an image by employing a genetic artificial intelligence technique for enhancing the quality of reconstructed images by recognizing patterns that are intrinsic to the images. This second embodiment may be used by itself or in combination with the first embodiment described above. It will be appreciated that computer-implemented method 220 may be a corollary to the functionality of the system 20, and may be performed by the system 20 or a suitable version thereof.

Again, initial steps, such as data acquisition steps, may be performed by the PET or SPECT imaging device 22 and involve software that is native to that device 22. These initial steps may include acquiring PET or SPECT image data, performing CT or line source attenuation correction, performing raw data corrections, and exporting the results to the system 20 and computer-implemented method 220 implementing the present technology. Further, the method may be implemented by a computer program implemented in the Java program language. Java may be used because of its cross platform compatibility, but the computer program may be implemented in substantially any suitable programming language, such as C++, C# or Basic, or scripting languages. This technique can also be implemented in CPU or GPU parallel processing techniques.

The paths of the input and output files may be set, as shown in 222. This may include defining the package, importing the libraries, defining the class, creating a "rand" class for making random numbers for pixel pairs, and setting the class to "main." The data may be read, as shown in 224. The data may be iteratively loaded from a binary file into an array or blocks of computer memory. The code may be read in as bytes, the bytes may be read into data, and a byte swap may be performed from little endian (Intel Processor Architecture) to big endian (Sun/Solaris Architecture) when source system data structure does not match the processing system architecture. The variables may be placed into the array. In more detail, this may include the following substeps. The array may be created to hold the data. The data may be read, and a while loop may be used to put the data into the array.

A defined number of initial pixel pairs may be created, and the average difference between pairs may be found, as shown in 226. The substeps for creating the pixel pairs may include creating an array to hold the pixel pairs, looping over all of the pixels and locating a random pair at a random angle from the original at a fixed distance, and calculating the difference between pixels. During the while loop, the mean value may be found for the difference between pairs. The lower half of the pixels may be eliminated. The eliminated pixels may be replaced with new pixels spawned from the remaining pairs. The new set of differences may be calculated.

In a mean elimination technique the average difference may be found between all of the pairs, the difference of each pair may be compared to this average difference between all of the pairs, as shown in 228. If the pair difference is less than the average difference, then the two pairs may be set to the average value between them, as shown in 230. However, if the pair difference is not less than the average difference, then a new child may be found, and the pair may be rechecked, as shown in 232. In more detail, the pixels may be compared with their respective pairs. If the pair has a difference less than the average, the average may be found between the two pairs and assigned to both. This greatly increases efficiency because the pairs do not need to be sorted. Otherwise, calculating the mean requires approximately n operations, and even the most efficient sorting algorithms only perform at n log(n), thereby increasing the speed of sorting by log(n). Once all pairs have passed the check, the new image may be exported to an output file, as shown in 234.

An embodiment of this demonstrated a significant acceleration in the AI filtering algorithm. The present technique required O(N) operations for the elimination step, where optimized sorting technique using a median prior to elimination resulted in O(N) log(N) operations and brute force sorting techniques required $O(N^2)$ operations prior to elimination. This acceleration enabled greater number of pixels pairs to be simulated and convergence times more acceptable to clinical operations.

In more detail, the scoring scheme may proceed as follows. Pairs may be created for each pixel and placed into a groups: survivors and eliminated. For each pixel that is eliminated, a new child pixel is spawned from an area of three-by-three or five-by-five pixels around a randomly chosen survivor.

An exemplary employment of the second computer-implemented method 220 may proceed substantially as follows. Alzheimer's disease is a neurodegenerative that accounts for about 60-80% of cases of dementia.

Florbetaben (18F) is used as a tracking agent to observe beta amyloid plaques in the brain. The tracker binds to the plaques and emits a positron that can be imaged with a PET scanner. These images show the locations of buildups in beta amyloid plaques in the brain. In normal gray matter, Florbetaben should wash out of the tissue, while in normal white matter, it should be retained. In a patient with Alzheimer's Disease, Florbetaben is beta amyloid clusters, which lowers the contrast between the gray and white matters. One problem with using purely qualitative data sets is that the grey and white matters are difficult to distinguish if there is poor contrast and resolution. This can lead to a misdiagnosis rate of 10-30%. Improving the image quality could improve the accuracy of diagnosis and perhaps aid in early detection of the disease before amyloid plaques have damaged the brain.

In this example, the examination of patients with known or suspected Alzheimer's disease may be facilitated by processing, analyzing, and displaying brain PET images. In particular, the embodiment uses a genetic AI technique to optimize the quality of PET scans of patients with Alzheimer's disease in order to increase the resolution, increase the contrast, and decrease the noise, including increasing the sharpness of edges and smoothing the areas of gray matter and white matter. Pairs of pixels may be collected, with each pair including a parent pixel and a child pixel within a radius of three to five pixels. The child pixel is eliminated from all pairs under the fifty percent mark. The eliminated child pixel may be replaced with a new pixels from the parent pixels. This may iterate over a number of iterations, such as between fifteen and twenty-five iterations, or twenty iterations, during which the algorithm may "learn" and improve the image.

In a test of this exemplary employment, images were used from five normal patients and five abnormal patients. A single transaxial slice at the cerebrum and pons (brain stem) was extracted. The AI image enhancement program was run for twenty iterations. The enhancement kernel may be extended three pixels, and those pairs with a difference greater than the mean difference may be rejected. New pairs may be spawned from the surviving pairs.

The technique did not introduce a bias into the data, and the mean values did not substantially change through the duration of the experiment, which indicates that the process itself was not changing the values, but was instead increasing the resolution and reducing the noise of the image. The mean value of the regions changed very little over every iteration in both the gray and white matter of the cerebrum and pons slices. The signal to noise ratio steadily improved with increasing iteration, which indicates that the overall noise was reduced successfully without the actual change of the content of the image. Edge sharpness also improved with increasing iteration, which demonstrates that as the program iterates, the resolution is improving. Thus, the technique demonstrated a steady improvement in the image quality with increasing iterations, and created a sharper image, increased the resolution, and increased the signal to noise without compromising the actual content of the image.

Figure 2:
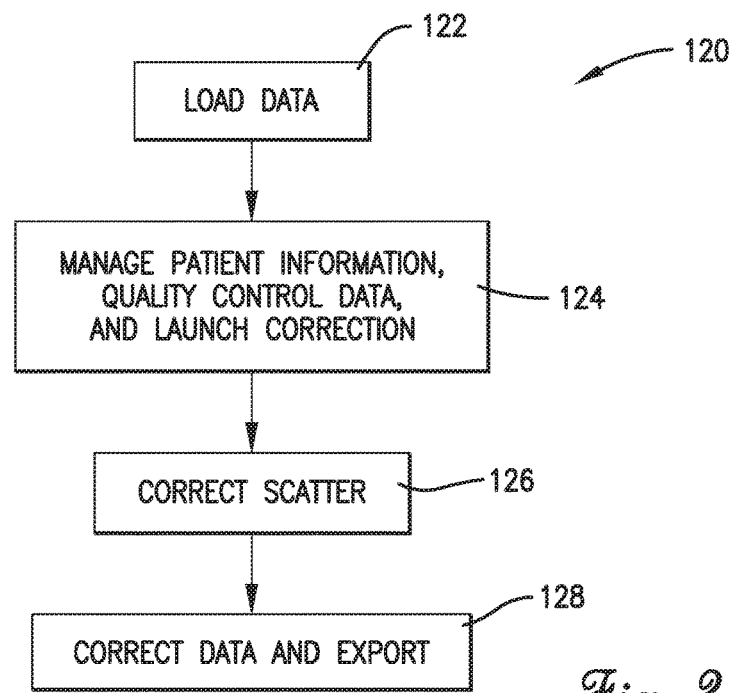
FIG. 2 is a flowchart of a first embodiment of a computer-implemented method for improving the quality of images, wherein the computer-implemented method may be performed by the system of FIG. 1.
Figure 3:
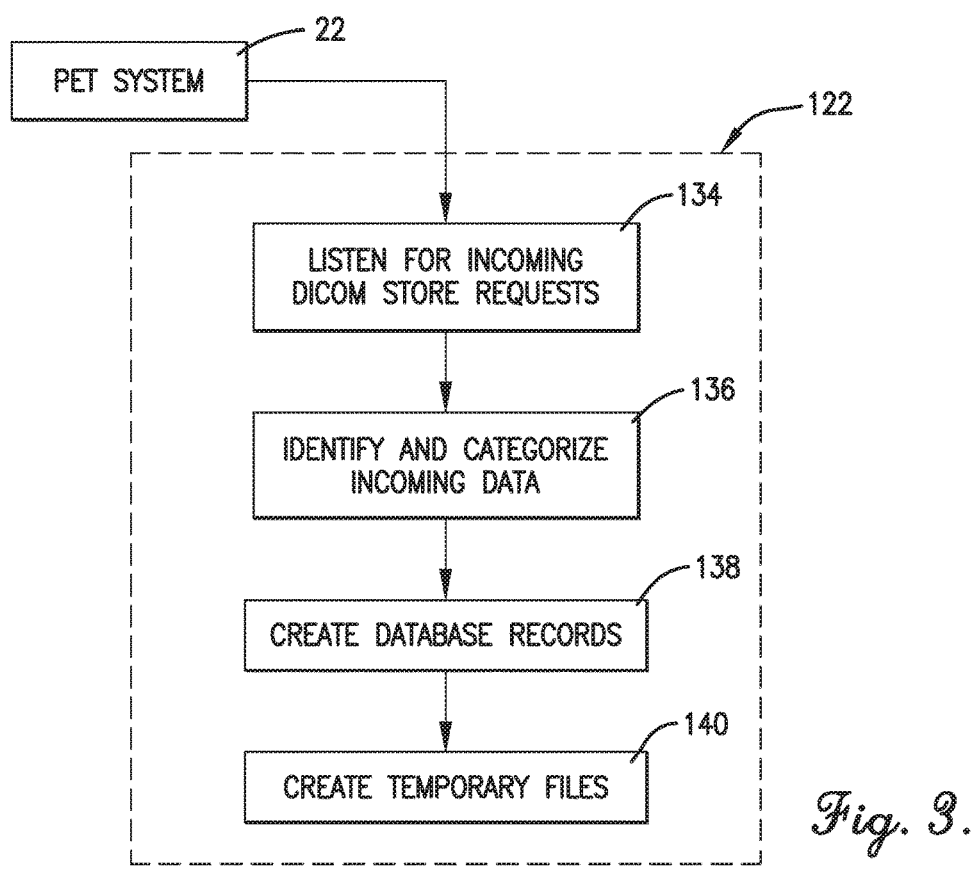
FIG. 3 is a flowchart of a data loading aspect of the computer-implemented method of FIG. 2.
Figure 4:
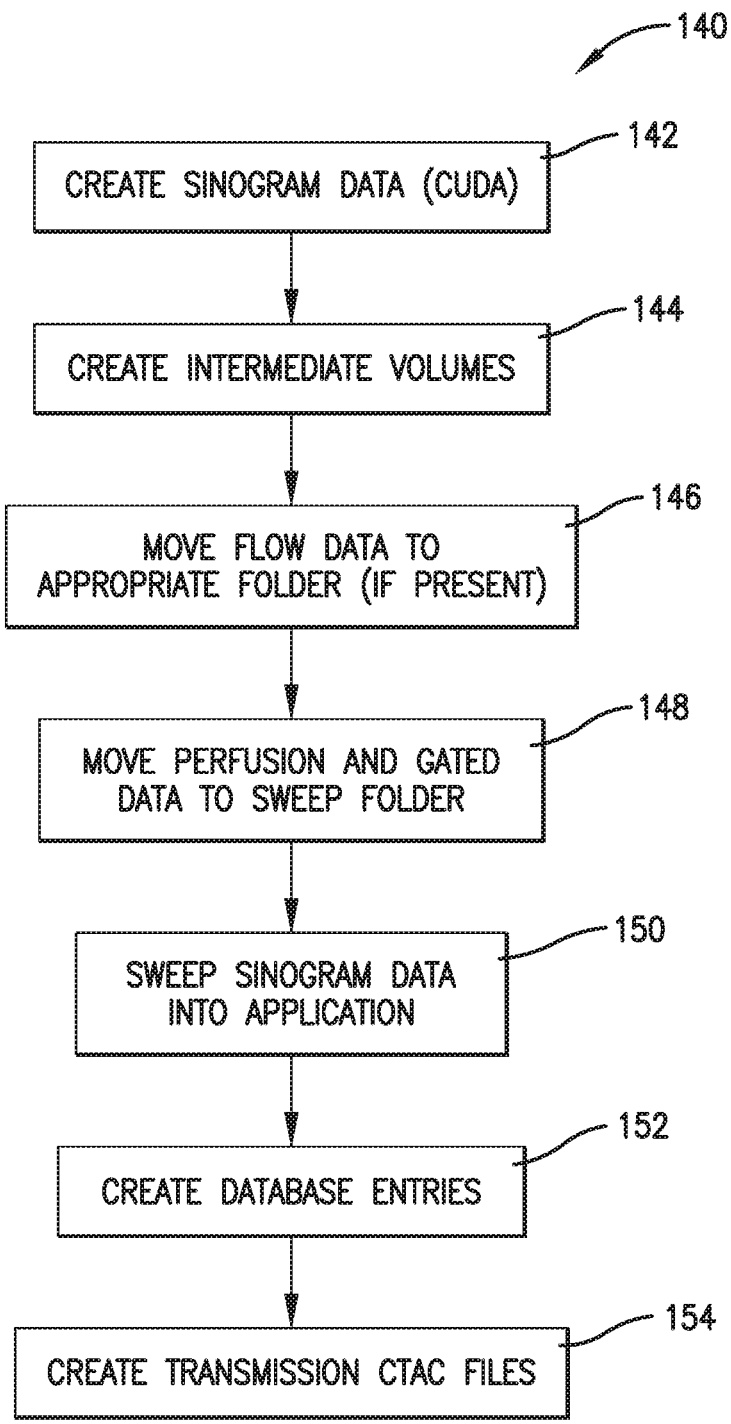
FIG. 4 is a flowchart of a temporary file creation aspect of the computer-implemented method of FIG. 3.

Referring to FIG. 2, the method 120 may broadly comprise data loading 122 (seen in more detail in FIGS. 3 and 4); patient management, data quality control, and correction launching 124 (FIG. 5); scatter correction 126 (FIG. 6); and data correction and export 128 (FIG. 7). In more detail, referring to FIG. 3, loading the raw data from the imaging device 22, from step 122, may include listening for incoming digital imaging and communications in medicine (DICOM) storage requests, as shown in 134. DICOM is a standard for handling, storing, printing, and transmitting information in medical imaging, and includes a file format definition and a network communications protocol. Loading the data may further include identifying and categorizing incoming data, as shown in 136, creating database records, as shown in 138, and creating temporary files, as shown in 140. Referring to FIG. 4, the creation of temporary files, from step 140, may include creating sinogram data, as shown in 142; creating intermediate volumes, as shown in 144; moving flow data to appropriate folders, as shown in 146; moving perfusion and gated data to a sweep folder, as shown in 148; sweeping the sinogram data into the application, as shown in 150; creating database entries, as shown in 152; and creating transmission CT-based attenuation correction (CTAC) files, as shown in 154.

Figure 5:
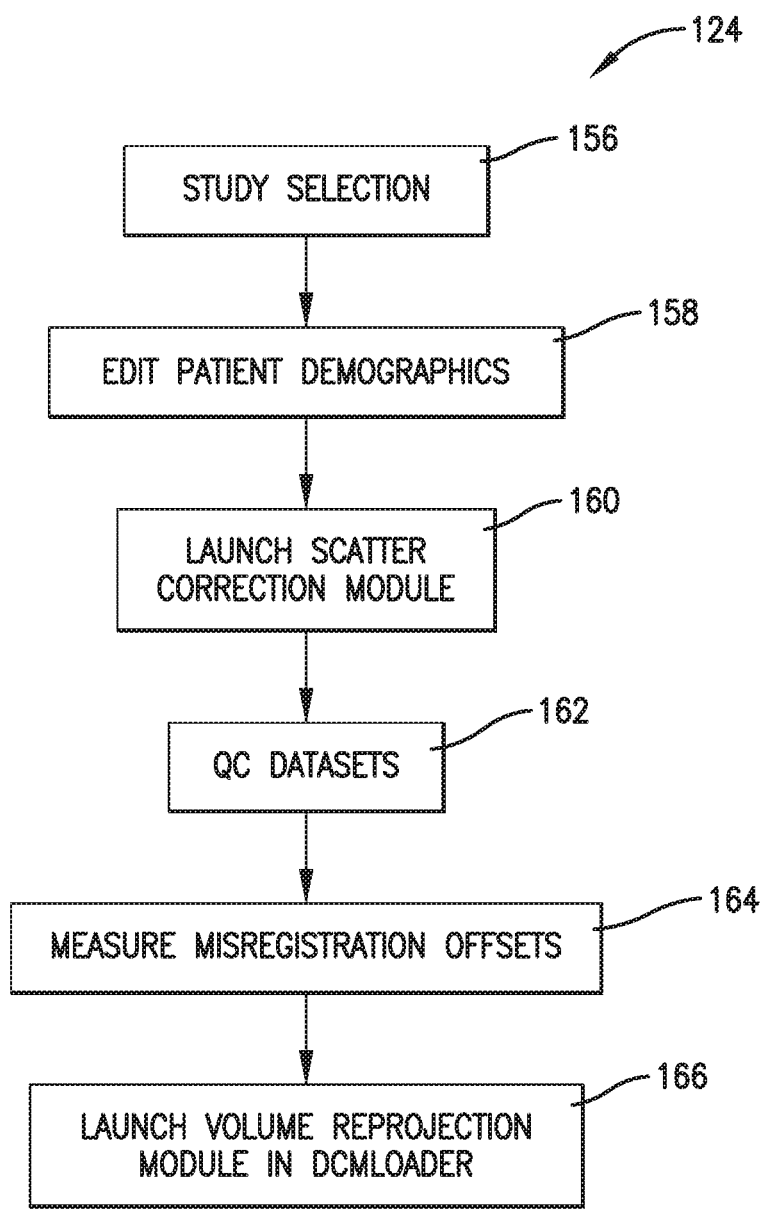
FIG. 5 is a flowchart of a quality control, study selection, and misregistration measurement aspect of the computer-implemented method of FIG. 2.

Referring to FIG. 5, the management of patient data, quality control of the data, and launching of correction, from step 124, may include selecting a study, as shown in 156; editing patient demographic information, as shown in 158; launching the scatter correction module, as shown in 160; quality controlling the datasets, as shown in 162; measuring the misregistration offsets, as shown in 164; and launching the volume reprojection module, as shown in 166.

The computer-implemented methods 120,220 may include more, fewer, or alternative actions, including those discussed elsewhere herein.

Although the invention has been described with reference to the one or more embodiments illustrated in the figures, it is understood that equivalents may be employed and substitutions made herein without departing from the scope of the invention as recited in the claims.

Having thus described one or more embodiments of the invention, what is claimed as new and desired to be protected by Letters Patent includes the following:

1. A computer-implemented method for improving the functioning of a computer for enhancing initial image data, the computer-implemented method comprising:
   loading the initial image data from an imaging device, including—
      sinogram data,
      intermediate volumes, and
      transmission computed tomography-based or line source attenuation correction files;
   performing scatter correction, including creating a scatter correction map and a scatter mask;
   measuring one or more misregistration offsets;
   creating a correction registration mask using volume reprojection;
   combining the correction registration mask with the scatter mask;
   applying the combined correction registration mask and scatter mask to correct the initial image data to create the enhanced image data;
   further enhance the enhanced image data using an AI based image enhancement technique; and
   communicating the enhanced image data to an interpretive application for display.

2. The computer-implemented method as set forth in claim 1, wherein the initial image data is generated by a medical imaging device, and the enhanced image data is used to diagnose a medical condition.

3. The computer-implemented method as set forth in claim 2, wherein the medical imaging device is a PET or SPECT imaging device.

4. The computer-implemented method as set forth in claim 1, wherein the correction registration mask is created using—
an attenuation corrected reconstructed emission dataset;
a non-attenuation corrected reconstructed emission data set; and
a computed tomography or line source attenuation map.

5. The computer-implemented method as set forth in claim 1, further including filtering the enhanced image data to reduce noise prior to communicating the enhanced image data to the interpretive application.

6. The computer-implemented method as set forth in claim 1, wherein performing scatter correction includes—
reconstructing an image space from the initial image data;
creating a probability field for a Monte-Carlo look-up;
employing a Monte-Carlo technique iteratively to simulate a first order scatter component from a scatter contaminated emission sonogram;
creating a random coincident event;
determining whether the coincident event is a prompt gamma;
following a progress of a photon as the photon is scattered or reaches an edge of an imaging field;
following a progress of the coincident photon until the coincident photon scatters or reaches an edge of the imaging field;
identifying each unscattered photon;
defining a new trajectory for each scattered photon that is not a prompt gamma, and following a progress of the photon on the new trajectory until the photon scatters or reaches the edge of the imaging field;
creating a random angle for each scattered photon that is a prompt gamma; and
creating a scatter estimate for each random event to compensate for scatter.

7. A computer-implemented method for improving the functioning of a computer for enhancing initial image data generated by a medical imaging device, the computer-implemented method comprising:
loading the initial image data from the imaging device, including creating temporary files, including—
sinogram data,
intermediate volumes, and
transmission computed tomography-based attenuation correction files;
performing scatter correction, including—
reconstructing an image space from the initial image data,
creating a probability field for a Monte-Carlo look-up,
employing a Monte-Carlo technique iteratively to simulate a first order scatter component from a scatter contaminated emission sinogram,
creating a random coincident event,
determining whether the coincident event is a prompt gamma,
following a progress of a photon as the photon is scattered or reaches an edge of an imaging field,
following a progress of the coincident photon until the coincident photon scatters or reaches an edge of the imaging field,
identifying each unscattered photon,
defining a new trajectory for each scattered photon that is not a prompt gamma, and following a progress of the photon on the new trajectory until the photon scatters or reaches the edge of the imaging field,
creating a random angle for each scattered photon that is a prompt gamma,
creating a scatter estimate for each random event to compensate for scatter, and
creating a scatter correction map and a scatter mask;
measuring one or more misregistration offsets;
creating a correction registration mask using volume reprojection;
combining the correction registration mask with the scatter mask;
applying the combined correction registration mask and scatter mask to correct the initial image data to create the enhanced image data; and
communicating the enhanced image data to an interpretive application for display and use in diagnosing a medical condition.

8. The computer-implemented method as set forth in claim 7, wherein the medical imaging device is a PET or SPECT imaging device.

9. The computer-implemented method as set forth in claim 7, wherein the correction registration mask is created using—
an attenuation corrected reconstructed emission dataset;
a non-attenuation corrected reconstructed emission data set; and
a computed tomography or line source attenuation map.

10. The computer-implemented method as set forth in claim 7, further including filtering the enhanced image data to reduce noise prior to communicating the enhanced image data to the interpretive application.

* * * * *